United States Patent [19]

Kita et al.

[11] Patent Number: 5,128,484

[45] Date of Patent: Jul. 7, 1992

[54] ACRYLONITRILE MALEIMIDES SOLUTION COMPOSITION OF IMPROVED SHELF LIFE AND METHOD FOR PRODUCTION THEREOF

[75] Inventors: Yuichi Kita, Akashi; Kazuo Kishino, Himeji; Masakazu Nakagawa, Himeji; Hitoshi Kanei, Himeji; Kentaro Sakamoto; Takeshi Okuno, both of Ibo, all of Japan

[73] Assignee: Sokubai Kagaku Kogyo, Co., Ltd., Osaka, Japan

[21] Appl. No.: 290,450

[22] Filed: Dec. 27, 1988

[30] Foreign Application Priority Data

Dec. 28, 1987 [JP] Japan ................ 62-329531
Aug. 17, 1988 [JP] Japan ................ 63-203124
Aug. 18, 1988 [JP] Japan ................ 63-203756
Aug. 18, 1988 [JP] Japan ................ 63-203757

[51] Int. Cl.$^5$ ............... C07D 207/448; C07D 207/452
[52] U.S. Cl. .................... 548/549; 548/548; 524/718
[58] Field of Search ............. 548/548, 549; 524/718

[56] References Cited

U.S. PATENT DOCUMENTS

| | | | |
|---|---|---|---|
| 4,786,738 | 11/1988 | Kita et al. | 548/548 |
| 4,851,547 | 7/1989 | Kita et al. | 548/549 |
| 4,904,803 | 2/1990 | Fujita et al. | 548/548 |
| 4,962,205 | 10/1990 | Kita et al. | 548/549 |

FOREIGN PATENT DOCUMENTS

| | | | |
|---|---|---|---|
| 2106075 | 5/1987 | Japan | 548/548 |
| 62-126167 | 6/1987 | Japan . | |
| 2126167 | 6/1987 | Japan | 548/548 |
| 2132854 | 6/1987 | Japan | 548/548 |
| 2138468 | 6/1987 | Japan | 548/548 |
| 2178567 | 8/1987 | Japan | 548/549 |

Primary Examiner—Robert L. Stoll
Assistant Examiner—John M. Covert
Attorney, Agent, or Firm—Omri M. Behr

[57] ABSTRACT

The present invention is directed to an acrylonitrile maleimides solution composition of highly desirable shelf like, having the acid component in said acrylonitrile maleimides soltuion adjusted to a level of no more than 0.1% by weight based on the amount of said maleimides contained in said solution and having a polymerization inhibitor in said solution adjusted to a level in the range of 0.0001 to 1% by weight based on the amount of said solution, and a method for the production thereof.

18 Claims, 1 Drawing Sheet

FIG.1

ACRYLONITRILE MALEIMIDES SOLUTION COMPOSITION OF IMPROVED SHELF LIFE AND METHOD FOR PRODUCTION THEREOF

BACKGROUND OF THE INVENTION

1. Field of the Invention

This invention relates to an acrylonitrile maleimides solution composition of improved shelf life and a method for the production thereof.

2. Description of the Prior Art

Maleimides are compounds useful as raw materials for synthetic resins, medicines, and agricultural pesticides. The maleimides which are solid at normal room temperature have been heretofore handled generally in various forms such as powder, flakes, and tablets. The maleimides in these forms contain minute particles of maleimides. While these maleimides in solid state are in transit, they undergo gradual comminution and give rise to minute particles of maleimides in a large amount.

The maleimides have undersirable qualities. They in themselves give a stimulus to human bodies. Particularly when their minute particles are inhaled, they stimulate the nasal cavities and the throats and incite coughs and sneezes. When their minute particles are suffered to adhere to the skins and remain there, they cause inflammation of the skins. When a person happens to handle maleimides containing such minute particles, he is required to take elaborate precautions to keep his skin from the maleimides.

In the circumstances, immense labor is expended for preventing the maleimides from shedding minute particles during the course of transportation or for removing minute particles from the maleimides after the transportation.

In most cases, solid substances are transported as stowed in paper bags, drums and containers. Persons engaging in any part of the work involved herein are inevitably exposed to the maleimides, with the natural result that minute particles of the maleimides adhere to their bodies.

At attempt at conveying solid substances by a pipeline for the purpose of precluding the solid substances from contacting human bodies is basically difficult. The solid substances in transit through the pipeline are apt to clog the interior of the pipeline. For the solid substances to be stably conveyed by the pipeline, harsh restrictions are imposed on the shape, size, specific gravity, etc. of the solid substances to be conveyed.

It is only safe to conclude that methods employed for transportation or conveyance of maleimides which are solid at room temperature entails various difficult problem. Similar problems are also encountered by methods to be employed for storage of the maleimides.

A method for conveying, transporting, or storing maleimides as a solution in acrylonitrile has been disclosed in Japanese Patent Laid-Open SHO 62(1987)-126,167. This method may well be called highly satisfactory in the sense that it can solve the problems mentioned above in the handling of maleimides.

The acrylonitrile maleimides solution in common use manifests heavy corrosiveness to metals. The phenomenon that such materials as carbon steel and stainless steel which are popularly used in industries are rapidly corroded by the acrylonitrile maleimides solution is observed frequently.

Moreover, this solution in storage generates an insoluble component therein tarnishes wholly in a blackish tint. This phenomenon of tarnishing entails a disadvantage that the maleimides are appreciably degenerated and consequently deprived of commercial value.

The desirability of developing an acrylonitrile maleimide solution relieved of heavy corrosiveness and improved in stability has been finding enthusiastic approval in the industry.

As one way of producing the acrylonitrile maleimides solution, there may be cited a method which comprises preparing a tank provided with a heating coil or a heating jacket and a stirrer, filling the tank with acrylonitrile to capacity, adding solid maleimides in the form of flakes, granules, or particles to the acrylonitrile, and then heating the resultant mixture by means of the heating coil or the heating jacket thereby dissolving the maleimides thoroughly in the acrylonitrile.

The solid maleimides assume various forms such as flakes, tablets, granules, and minute particles as described above. Without maleimides possess a quality such that, while the solid maleimides are in storage, their individual particles coalesce and form very hard lumps.

These solid maleimides are generally stored as stowed in paper bags, plastic bags, drums, and containers. During their storage, however, they are transformed into large hard lumps owing to the aforementioned quality peculiar to the solid maleimides.

When such lumps of solid maleimides are to be dissolved in acrylonitrile, these lumps in process of conveyance from their containers to a maleimides dissolving tank (hereinafter referred to simply as "dissolving tank") are suffered to clog a nozzle for injection of the solid maleimides into the dissolving tank and consequently disrupt the operation of dissolution.

Further, the dissolution of the solid maleimides in acrylonitrile proceeds with large absorption of heat and, therefore, requires the contents of the dissolving tank to be heated to ensure safe dissolution.

The inevitable formation of such large, lumps obstructs effective control of the introduction of the solid maleimides into the dissolving tank. When the feed rate of the solid maleimides into the dissolving tank is unduly lowered, the liquid temperature inside the dissolving tank is heavily fluctuated.

Owing to this heavy fluctuation of the inner temperature of the dissolving tank, the acrylonitrile maleimides solution once formed is compelled to induce precipitation of crystals of maleimides in a large volume. When the lumps of maleimides happen to enter the dissolving tank in a large amount at once, the heat imparted to the solution by the heating falls short of reaching the level required for dissolving the maleimides, with the result that the lumps of solid maleimides remain intact within the dissolving tank.

When this situation arises, the dissolving tank is no longer capable of continuing the operation of stirring which is indispensable to the work of dissolution. Then, the lumps cannot be dissolved. There are times when the failure of the dissolving tank to stir the inner liquid thereof entails local heating of the part of the inner liquid approximating to the surface of heating and brings about serious consequences such as, for example, polymerization of the solution.

The operation of dissolution under discussion is generally carried out at a high temperature close to the boiling point of acrylonitrile. As widely known, acrylonitrile is an extremely flammable compound and the acrylonitrile vapor, on mixture with the air, readily produces an explosive gas.

As mentioned above, the solid maleimides are stowed in returnable containers, drums, paper bags, and plastic bags. These containers do not easily permit thorough displacement of the air entrapped therein with an inert gas. When the solid maleimides are released from such containers as mentioned above and introduced into the dissolving tank to be dissolved in acrylonitrile therein, the air existing in the gaps between the individual particles of the solid maleimides is inevitably entrained by the solid maleimides and allowed to mingle with acrylonitrile and give rise to the explosive gas.

The existing methods available for the dissolution of solid maleimides in acrylonitrile do not deserve to be called perfect in the strict sense of the word.

The circumstances quite aptly urge the development of a method which produces an acrylonitrile maleimides solution without entailing any of the drawbacks mentioned above.

An object of this invention, therefore, is to provide an acrylonitrile maleimides solution of improved shelf life and a method for the production thereof.

Another object of this invention is to provide a method for producing an acrylonitrile maleimides solution easily without exposing human bodies to minutes particles of maleimides.

A further object of this invention is to provide a method for producing an acrylonitrile maleimides solution even from solid maleimides which have coalesced by change into coarse lumps during storage.

SUMMARY OF THE INVENTION

The objects described above are accomplished by an acrylonitrile maleimides solution composition of highly satisfactory shelf life, which composition has the acid content in the acrylonitrile maleimides solution adjusted to no more than 0.3% by weight based on the amount of maleimides contained in the solution and the polymerization inhibitor content in the solution adjusted in the range of 0.0001 to 1% by weight based on the amount of the solution.

These objects are further accomplished by a method for the production of an acrylonitrile maleimides solution composition, which method comprises placing solid maleimides in a substantially airtight closed container provided with liquid circulating nozzles and circulating heated acrylonitrile through the solid maleimides in the presence of a polymerization inhibitor via the nozzles thereby dissolving the maleimides.

The objects are also accomplished by a method for the production of an acrylonitrile maleimides solution composition, which method comprises placing solid maleimides in a substantially airtight closed container provided with liquid circulating nozzles one each in the upper and lower parts thereof, adding acrylonitrile to the solid maleimides in the presence of a polymerization inhibitor, and heating the acrylonitrile solution withdrawn via the upper nozzle of the container and circuiting the heated acrylonitrile solution into the interior of the container via the lower nozzle of the container thereby dissolving the maleimdies.

The objects are accomplished by a method for the production of an acrylonitrile maleimides solution composition, which method comprises either placing preliminarily loosed solid maleimide blocked particles in an airtight closed container or crushing solid maleimides in an airtight closed container, and in a state retaining a substantially inert atmosphere continuously or intermittently introducing the loosed solid maleimides blocked particles from the container into a dissolving tank thereby allowing the maleimides to be dissolved in acrylonitrile therein.

EXPLANATION OF THE PREFERRED EMBODIMENT

The inventors have continued a diligent study with a view to developing an acrylonitrile maleimides solution composition free from corrosiveness to metals and excellent in stability. We have found that acrylonitrile itself and an acrylonitrile maleimides solution of high purity possess no corrosiveness to metals. After a study on various corrosive impurities present in maleimides, we have found that the acid component in maleimides forms a cause for the corrosion of metals. It has been found quite unexpectedly that the stability of the acrylonitrile maleimides solution is significantly affected by the amount of the acid component in maleimides.

It has been found that the corrosiveness to metals and the poor stability exhibited by the acrylonitrile maleimides solution are caused by the acid component in the maleimides and that the maleimides having a small acid component content can exist very stably in the presence of a polymerization inhibitor. The present invention has been perfected as the result. To be specific, this invention is directed to an acrylonitrile maleimides solution composition highly satisfactory in shelf life, having the acid component in the acrylonitrile maleimides solution adjusted to a level of no more than 0.3% by weight based on the amount of the maleimides contained in the solution and having a polymerization inhibitor incorporated in the solution in an amount in the range of 0.0001 to 1% by weight based on the amount of the solution.

The maleimides to which the transferring and storaging method of this invention can be effectively applied are the compounds represented by the general formula I:

wherein R stands for one member selected from the class consisting of hydrogen atom, an alkyl group of 1 to 20 carbon atoms, phenyl group, benzyl group, cyclohexyl group, pyridyl group, quinolyl group, and the groups mentioned above severally having a halogen substitution, a carboxyl group substitution, or nitro group substitution, preferably alkyl groups or phenyl group. Typical examples of these compounds include maleimide, N-methyl maleimide, N-ethyl maleimide, N-hexyl maleimide, N-octyl maleimide, N-dodecyl maleimide, N-benzyl maleimide, N-cyclohexyl maleimide, N-phenyl maleimide, N-nitrophenyl maleimide, N-methoxyphenyl maleimide, N-methylphenyl maleimide, N-carboxyphenyl maleimide, N-hydroxyphenyl maleimide, N-chlorophenyl maleimide, N-dimethylphenyl maleimide, N-dichlorophenyl maleimide, N-bromophenyl maleimide, N-dibromophenyl maleimide, N-trichlorophenyl maleimide, and N-tribromophenyl maleimide.

The acid component present in the maleimides is an acid catalyst to be used in the production of maleimides or an impure substance to be by-produced in the production of maleimides. Examples of the acid catalyst are inorganic or organic acids such as sulfuric acid, p-toluenesulfonic acid, benzenesulfonic acid, orthophosphoric acid, pyrophosphoric acid, metaphosphoric acid, and trichloroacetic acid and examples of the impure substance are maleic acid, fumaric acid, maleinamic acid, and fumaramic acid.

When the maleimides are produced by a method of effecting dehydroimidation of maleinamic acid by use of a carboxylic anhydride such as acetic anhydride, the acetic acid which is by-produced by the reaction with the formed water is also contained in the produced maleimides. Though the amount of the acid component is generally varied by the method used for purification of maleimides, it normally falls in the range of 0.01 to 5% by weight based on the amount of produced maleimides.

To prevent the acrylonitrile maleimides solution from corroding metals and relieve of the acrylonitrile maleimides solution of inferior stability, the acid component in the maleimides must be lowered to a level of no more than 0.3% by weight, preferably no more than 0.2% by weight. The decrease of the acid component in the maleimides may be attained, for example, by a method which purges the maleimides of the acid component by thorough washing with water or a method which curbs the by-production of acidic impurities by selection of the reaction conditions in the production of maleimides.

For the production of maleimides, a method which effects dehydroimidation of maleinamic acids by use of acetic anhydride and a method which effects dehydroimidation of maleinamic acid in acrylonitrile by use of acetic anhydride are available, for example. By any of these methods which involve the use of acetic anhydride, it is extremely difficult to lower the acid component in the produced maleimides to a level of no more than 0.3% by weight even when the product is thoroughly washed with water or an alkali. For the product by any of these methods to be stably stored on a commercial scale, there are problems yet to be solved. The maleimides which are produced by a method which effects their synthesis in an organic solvent in the presence of an acid catalyst are rather desirable in the sense that the removal of the acid component is easy to make. As a more desirable way, a method which refines the maleimides produced as described above to a high level of purity by washing them with water and further distilling the washed maleimides may be cited. These are not the only methods available for the removal of the acid component.

The polymerization inhibitors which can be used in the dissolution of solid maleimides in acrylonitrile include methoxybenzoquinone; p-methoxyphenol; phenothiazine; hydroquinone; alkylated diphenylamines; methylene blue; tert-butyl catechol; tert-butylhydroquinone; dialkyl dithiocarbamates such as zinc dimethyldithiocarbamate, copper dimethyldithiocarbamate, and copper dibutyldithiocarbamate; thiodipropionic esters; mercaptobenzimidazole; triphenyl phosphites; alkylphenols; and hindered phenols such as 2,4-bis(n-octylthio)-6-(4-hydroxy-3,5-di-t-butylanilino)-1,3,5-triazine; 2,2'-thiobis-(4-methyl-6-t-butylphenol) and triethylene glycol bis-[3-(3-t-butyl-5-methyl-4-hydroxyphenyl)-propionate], for example. The amount of the polymerization inhibitor to be used is in the range of 0.0001 to 1% by weight, preferably 0.001 to 0.5% by weight, based on the amount of the acrylonitrile maleimides solution. The particular kind of the polymerization inhibitor to be used is selected in due consideration of the kind of the polymer to be produced, the method of polymerization, and the initiator to be used. Particularly when the finished product of a styrene type resin such as ABS resin or an AS resin is desired to be a polymer abounding in whiteness, hindered phenols are used effectively as a polymerization inhibitor. The addition of the polymerization inhibitor may be effected by being dissolved in advance in acrylonitrile or by being directly mingled with solid maleimides.

For a certain known reason, the polymerization inhibitor is believed to manifest an action of effectively curbing the occurrence of coloring impurities in the finished product in the acrylonitrile maleimides solution or during the course of polymerization.

The concentration of maleimides in the acrylonitrile maleimides solution is selected in consideration of the kinds of the final polymer to be obtained by use of the acrylonitrile maleimides solution, the method of polymerization, and the conditions for the polymerization. Generally, this concentration is in the range of 30 to 90% by weight, preferably 40 to 70% by weight. The dissolution of maleimides in acrylonitrile can be attained basically by any of the conventional methods available for the purpose. It may be effected by throwing acrylonitrile into maleimides or allowing maleimides to dissolve an acrylonitrile. The maleimides to be used in this case may be in a solid state or in a molten liquid state. The temperature of the solution thus obtained by the dissolution is generally in the range of 10° to 70° C., though it is variable with the concentration of maleimides in the solution. During the course of this dissolution, the vapor phase in the reaction system is desired to be displaced with nitrogen and may be maintained under normal pressure.

This invention is further directed to a method for the production of an acrylonitrile maleimides solution, which comprises placing solid maleimdies in a substantially airtight closed container provided with liquid circulating nozzles and circulating heated acrylonitrile solution through the solid maleimides in the presence of a polymerization inhibitor via the liquid circulating nozzles thereby dissolving the maleimides.

The solid maleimides may be in any of the forms of flakes, granules, and minute particles. Preferably, they are in the form of flakes.

It has been found that the minute particles in maleimides which pose problems as mentioned above are preferentially dissolved in acrylonitrile in accordance with the method of the present invention.

Commonsensically it is inferred that when a solid substance is brought into contact with a solvent, the solid substance is not easily dissolved in the solvent because the individual particles of the solid substance coalesce face to face and form large lumps or shed from the solid substance are headed in the intervening gaps to the extent of rendering difficult the passage of the solvent through the gaps. It is surprising to note that in the case of the combination of maleimides and acrylonitrile, the acrylonitrile solution can be easily passed through the gaps between the individual particles and, therefore, the solid maleimides are very easily dissolved in acrylonitrile.

The maleimides are highly susceptible to polymerization and, even during their dissolution in acrylonitrile, they readily induce polymerization. It has been found, however, that this polymerization can be effectively prevented by the presence of the polymerization inhibitor in the reaction system.

It is literally an amazing fact that by the method of this invention, the acrylonitrile maleimides solution can be economically produced perfectly and easily without entailing the occurrence of minute particles of maleimides. It is only proper to conclude that the present invention constitutes itself a remarkable advance in the production of the solution.

The airtight container to be used for the purpose of the dissolution has no particular restriction but has to be provided with liquid-circulating nozzles. To be specific, either a stationary tanks such as, for example, a tank provided with an internal heating coil or a jacketed tank or a mobile tank such as, for example, a tank car, a tank lorry, or a bulk container may be used.

The density to which the container is packed with the maleimides is in the range of 0.2 to 0.8 ton/m$^3$, preferably 0.3 to 0.7 ton/m$^3$.

The application of heat to the acrylonitrile in circulation may be attained by means of a heat exchanger to be disposed on the outside of the container or a heating jacket or a heating coil to be attached as an accessary to the container, for example.

The temperature of the acrylonitrile solution to be circulated during the course of dissolution is generally set at a level about 10° to 30° C. higher than the saturated solution temperature corresponding to the concentration of maleimides in the solution, though it is variable more or less with the concentration of maleimides in the acrylonitrile maleimides solution.

The amount of the solution to be circulated during the dissolution of maleimides is generally set at a level such that the contents of the dissolution tank are wholly renewed 0.1 to 10 times per hour, though it is variable with such factor as the diameter of the pipe and the capacity of the liquid circulating pump.

The concentration of the acrylonitrile maleimides solution to be produced is suitably selected. It is not particularly limited for the purpose of this invention. For the sake of the transportation or storage of maleimdes in the form of a solution in acrylonitrile, this concentration is desired to be high. In this case, the concentration is in the range of 30 to 90% by weight.

As one preferred embodiment of this invention, there may be cited a method which accomplishes the production of an acrylonitrile maleimides solution by packing a mobile tank such as a tank lorry or a bulk container with maleimides in the form of flakes, transporting the solid maleimides to a given destination, filling the container with acrylonitrile and a polymerization inhibitor, and then heating and circulating the acrylonitrile through the interior of the tank.

By this method of the present invention, the tank lorry or bulk container is not required to be provided with any special heat insulating device adapted to prevent the maleimides from being precipitated in the acrylonitrile maleimides solution. Further, the maleimides in transit are precluded from deterioration. The transportation and the handling of the maleimides are attained easily and economically. This method proves to be advantageous in many respects.

This invention is also directed to a method for the production of an acrylonitrile maleimides solution, which comprises placing solid maleimides in a substantially airtight closed container provided with liquid circulating nozzles one each in the upper and lower parts thereof, adding acrylonitrile to the solid maleimides in the presence of a polymerization inhibitor, and then withdrawing acrylonitrile solution from the container via the upper nozzle and heating the acrylonitrile solution and, . at the same time, circulating the heated acrylonitrile through the container interior via the lower nozzle thereby dissolving the maleimides.

In place of this method, there may be conceived a method which effects the dissolution of maleimides by withdrawing the acrylonitrile solution from the container via the lower nozzle and circulating the heated acrylonitrile solution into the container via the upper nozzle. The acrylonitrile maleimides solution which is retained inside the container, however, has widely different concentration in the upper layer and the lower layer and forms a supersaturated solution in the lower layer.

When the solution in the lower layer region is withdrawn via the lower nozzle, therefore, the maleimides are precipitated in the form of crystals near the lower nozzle and are suffered to clog the lower nozzle and consequently deprive it of its function for permitting release of liquid. In accordance with the method of this invention which effects the circulation of the solution by withdrawing this solution from the upper layer region via the upper nozzle and returning the heated solution to the lower layer region via the lower nozzle, the occurrence of crystals of maleimides near the nozzles is not observed at all and the clogging of the nozzles with the precipitated crystals is absolutely nil because the solution withdrawn via the upper nozzle is an unsaturated solution.

Fortunately, the possibility of crystals being precipitated in the regions adjacent to the nozzles is totally absent because the inflow of the solution via the lower nozzle lends itself to diluting the dense supersaturated solution present in the proximity of the lower nozzle and giving rise to an unsautrated solution.

It has been consequently found that the acrylonitrile maleimides solution can be easily produced by withdrawing the solution from the upper layer region, heating the solution as by passage through a heat exchanger and circulating the heated solution into the container interior via the lower nozzle. The maleimides are highly susceptible to polymerization and readily induce polymerization even during the dissolution thereof in acrylonitrile. It has been found, however, that the polymerization of the maleimides can be effectively prevented by carrying out the dissolution in the presence of a polymerization inhibitor.

Generally when a solid substance is brought into contact with a solvent, the individual particles of the solid substance coalesce and form large lumps or the minute particles shed from the solid substance are suffered to heat in the intervening gaps between the individual particles possibly to an extent of rendering difficult the passage of the solvent through the intervening gaps. There is also a possibility that crystals precipitated near the outlet nozzle clog the nozzle and render the release of liquid therethrough difficult. Thus, it is very difficult to dissolve a solid substance and obtain a solution thereof by causing a solvent to be circulated through a packed bed of the solid substance. Moreover, in the case of the maleimides which are a polymerizing substance, the polymerization possibly induced during the course of dissolution forms a cause for troubles.

The method which produces a solution of a polymerizing solid substance by packing the substance in a container and circulating a solvent through this container has not been accepted as a useful method.

It is truly an amazing fact that by the method of this invention, the acrylonitrile maleimides solution can be produced economically and safely by enabling the solid maleimides, a substance highly susceptible to polymerization, to be dissolved very easily in acrylonitrile without entailing the occurrence of minute particles of maleimides.

The airtight closed tank to be used for the dissolution is not required to be in any special form but is only required to be provided with liquid circulating nozzles one each in the upper part and the lower part thereof. To be specific, either a stationary tank such as, for example, a tank provided with an internal heating coil or a tank provided with a heating jacket or a mobile tank such as, for example, a tank car, a tank lorry, a bulk container may be used.

The density of the packing of the maleimides in the container, the method for heating the acrylonitrile in process of circulation, the temperature of the acrylonitrile solution, the amount of the solution to be circulated for the dissolution of the maleimides, and the concentration of maleimides in the acrylonitrile maleimides solution are as described above.

This invention is further directed to a method for the production of an acrylonitrile maleimides solution, which comprises either placing preparatorily loosed solid maleimides blocked particles in an airtight closed container or crushing solid maleimides inside the airtight closed container and then, in a state retaining a substantially inert atmosphere, continuously or intermittently introducing the maleimides from the container into a dissolving tank to be dissolved in acrylonitrile therein.

After a study, we have found that though the solid maleimides in storage have a quality such that their individual particles coalesce and form a large lumps, this transformation into the large lumps proceeds very slowly and that, therefore, when the large lumps of the loosed solid maleimides blocked particles mentioned above are crushed and transformed into ordinary flakes, tablets, or granules, they can be easily handles, though in a short span of time. We have further found that the atmosphere surrounding loosed solid maleimides blocked particles can be readily displaced with the atmosphere of an inert gas such as nitrogen gas and that when the maleimides are dissolved in acrylonitrile or after the dissolution, the composition of the gaseous phase over the solution can be easily adjusted to fall outside the explosive limits. This knowledge has also been incorporated in the present invention.

Figure 1:
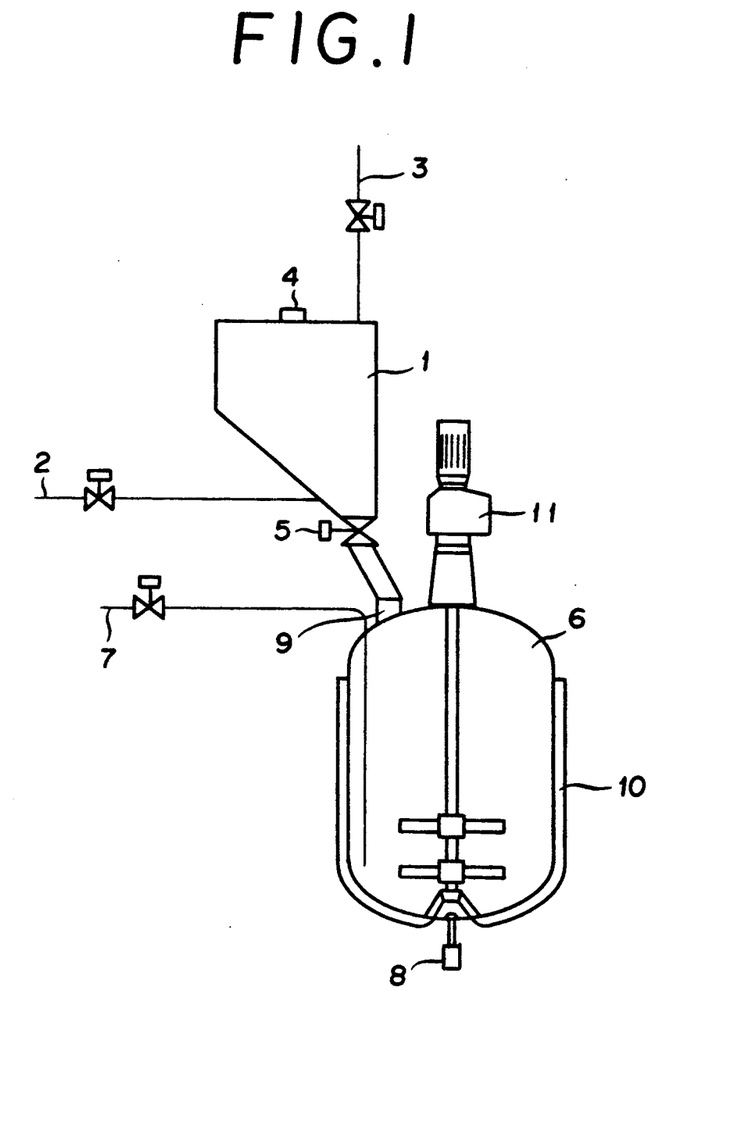
FIG. 1 is a schematic diagram illustrating a typical maleimides dissolving apparatus to be used in working the method for the production of an acrylonitrile solution according to the present invention.

Now, the present invention will be described in detail below with reference to FIG. 1 which illustrates a typical apparatus for the dissolution of maleimides.

In this invention, the solid maleimides which are stored as stowed in a paper bag, a plastic bag, or a returnable container are loosed in blocked particles in advance of their introduction into a maleimides dissolving tank 6 and then packed in an airtight closed container 1 annexed to the dissolving tank 6. Otherwise, the solid maleimides are loosed in blocked particles within the airtight closed container and then introduced into the dissolving tank 6. This crushing of the solid maleimides can be accomplished by any of conventional method available for the purpose.

After the solid maleimides have been transferred from the container such as a paper bag into the airtight closed container 1, the air entrapped in the airtight closed container 1 is displaced with an inert gas such as nitrogen, carbon dioxide, or argon through the medium of nozzles 2 and 3 attached to the airtight closed container 1.

After the operation mentioned above, the loosed solid maleimides blocked particles are delivered continuously or intermittently from the airtight closed container 1 into the dissolving tank 6. Thus, by the method of this invention, the acrylonitrile solution can be produced quite safely without suffering the lumps of solid maleimides to go to clogging a maleimides discharge outlet 5 or suffering the acyrylonitrile to mingle with air and give rise to an explosive gas. The dissolving tank 6 used for the dissolution of solid maleimides is provided with a heat coil or heating jacket 10 and a stirrer 11. Generally it is further provided with a solid maleimides inlet nozzle 9 and an acrylonitrile maleimides solution outlet 8. The airtight closed container 1 attached to the dissolving tank 6 is provided with a solid maleimides inlet 4 and on the underside thereof with a solid maleimides discharge outlet 6. Generally, it is further provided with an inert gas inlet nozzle 2 and an outlet nozzle 3 because the airtight closed container requires the air entrapped therein to be displaced with an inert gas.

For the displacement of the entrapped gas in the airtight closed container with the inert gas to be carried out easily, the container is desired to be constructed so as to retain necessary airtightness. Specifically, the airtightness is ensured by providing the solid maleimides inert and discharge outlet, the discharge outlet, and the inert gas nozzles each with a stop valve.

It is provided, when necessary, at the solid maleimides inlet with a device for crushing large lumps of solid maleimides (not shown). Where the feed rate of the solid maleimides is required to be controlled rigidly, the airtight closed container may be provided at the solid maleimides discharge outlet with a rotary valve. The airtight closed container may be made of any material which is only required to be capable of withstanding the action of acrylonitrile vapor and maleimides. Desirably, it is made of aluminum, stainless steel, or carbon steel, for example.

The dissolution is desired to be accomplished by filling the dissolving tank in advance with heated acrylonitrile and then introducing the solid maleimides into the acrylonitrile held in the tank. Of course, this particular sequence of procedure is not critical. The temperature of the contents of the dissolving tank during the course of dissolution is generally set in the range of 10° to 70° C., preferably 20° to 60° C., though it is variable with the concentration of the acrylonitrile maleimides solution. The speed of the introduction of solid maleimides into acrylonitrile is generally in the range of 1 to 1,000 kg of solid maleimides per ton of acrylonitrile per minute, though variable with the amount of heat applied to the solution by heating. It is selected in due consideration of the inner volume of the dissolving tank, the diameter of the inlet, the inner volume of the hopper, etc.

The present invention, as described above, concerns an acrylonitrile maleimides solution which has the acid component in the acrylonitrile maleimides solution adjusted to a level of no more than 0.3% by weight based on the amount of the maleimides contained in the solution and has the polymerization inhibitor adjusted to a level in the range of 0.0001 to 1% by weight based on the amount of the solution. Since carbon steel or stainless steel, a general purpose industry grade material, can be used as the material for the storing container, the apparatus for handling is not expensive. The tank lorry, tank car, or bulk container which is utilized for the transportation of the solution is not required to be made of any special material but may be made of a general-purpose ordinary material. Thus, the solution can be carried out inexpensively. Particularly since the acrylonitrile maleimides solution can be stably handled and prevented from deterioration during storage, the final polymer produced from the maleimides enjoys high quality. As described above, by the method of this invention, the maleimides can be produced and supplied inexpensively and safely.

Further, since the method of this invention is as described above, it enjoys the following advantages.

(1) The acrylonitrile maleimides solution can be produced safely and easily without entailing the occurrence of harmful minute particules of maleimides or the exposure of human bodies to the maleimides.

(2) Since the acrylonitrile maleimides solution can be produced with a very simple apparatus, the produced acrylonitrile maleimides solution is not expensive.

(3) The acrylonitrile maleimides solution can be prepared immediately before its actual use by the procedure which comprises transporting the maleimides to the destination as stowed in a mobile tank such as a tank lorry or a bulk container and dissolving the maleimides in acrylonitrile there. Since the trouble due to the otherwise inevitable precipitation of maleimides in transit can be precluded, therefore, the acrylonitrile maleimides solution can be obtained inexpensively and simply.

(4) The acrylonitrile maleimides solution can be easily produced from the solid maleimides which have been transformed into large lumps during storage.

(5) The solid maleimides to be effectively used in the present invention are never discriminated on account of the type of the storing container to be used.

(6) The operation of dissolving the solid maleimides in acrylonitrile is performed very easily because the speed of introduction of the solid maleimides into the dissolving tank can be freely controlled.

(7) The solution can be produced with great safety because the acrylonitrile is not suffered to single with the air and form an explosive gas.

(8) The acrylonitrile maleimides solution can be produced inexpensively with a simple apparatus.

Now, this invention will be described more specifically below with reference to working examples.

EXAMPLE 1

| N-phenyl maleimide composition | |
|---|---|
| N-phenyl maleimide | 99.9% by weight |
| N-phenyl maleinamic acid (molecular weight 191) | 0.1% by weight |
| Total acid component (only N-phenyl maleinamic acid) | 0.1% by weight |

When the inner temperature of the flask was set to 50° C. by adjusting the temperature of the bath, the maleimides where immediately dissolved to give rise to a perfectly clear yellow acrylonitrile maleimides solution. With the temperature of the water bath further adjusted, a test piece of carbon steel measuring 20 mm × 40 mm × 2 mm was left standing in the solution at an inner temperature of 50° C. for 30 days. At the end of this standing of the test piece in the solution, the solution was found to retain the original clarity intact or contain absolutely no foreign matter. The test piece of carbon steel showed absolutely no discernible sign of corrosion. When the solution was subjected to distillation under a vacuum to expel acrylonitrile, there remained bright yellow crystals.

By liquid chromatography, the crystals were found to have a purity of 99.9% by weight and absolutely no sign of deterioration.

Control 1

The procedure of Example 1 was faithfully repeated, except that N-phenyl maleimide adjusted to the following composition was used instead.

| N-phenyl maleimide composition | |
|---|---|
| N-phenyl maleimide | 99.5% by weight |
| N-phenyl maleinamic acid (molecular weight 191) | 0.1 by weight |
| Phosphoric acid | 0.2 by weight |
| Maleic acid | 0.2 by weight |
| Total acid component | 0.5 by weight |

When this solution was left standing similarly at 50° C. for 30 days, it turned brown, formed insolubles in a large amount, and completely lost the clarity. The surface of the test piece of carbon steel lost the initial metallic gloss and showed a clear sign of corrosion. When the solution was distilled to expel acrylonitrile, there remained a yellowish brown solid substance.

By liquid chromatography, this solid substance was found to have a purity of 95.3% by weight and a clear sign of deterioration.

Control 2

The procedure of Example 1 was faithfully repeated, except that N-phenyl maleimide adjusted to the following composition was used instead.

| N-phenyl maleimide composition | |
|---|---|
| N-phenyl maleimide | 99.2% by weight |
| N-phenyl maleinamic acid | 0.05 by weight |
| Acetic acid | 0.3 by weight |
| Maleic acid | 0.05 by weight |
| Total acid component | 0.4 by weight | tallic gloss and showed a clear sign of corrosion. When this solution was distilled to expel acrylonitrile, there remained a light yellowish brown solid substance. By liquid chromatography, this solid substance was found to have a purity of 97.2% by weight and a clear sign of deterioration.

EXAMPLES 2 TO 14 AND CONTROL 3

The procedure of Example 1 was repeated, except that N-phenyl maleimide adjusted to the following composition was used instead maleimide adjusted to the following composition was used instead and the kind and amount of a polymerization inhibitor were changed as indicated in Table 1 and the inner temperature of the flask was changed to 70° C. The results are shown in Table 1.

| N-phenyl maleimide composition | |
|---|---|
| N-phenyl maleimide | 99.8% by weight |
| N-phenyl maleinamic acid | 0.1% by weight |
| Maleic acid | 0.1% by weight | and severally using triethylene glycol bis[3-(3-t-butyl-5-methyl-4-hydroxyphenyl)propionate], and p-methoxyphenol as a polymerization inhibitor. They were left standing at 70° C. for 30 days by way of a test for stability. The results are shown in Table 2.

| N-phenyl maleimide composition | |
|---|---|
| N-phenyl maleimide | 99.85% by weight |
| N-phenyl maleinamic acid | 0.1% by weight |
| Maleic acid | 0.05% by weight |

TABLE 2

| | | | Polymerization inhibitor | | Before standing | | After standing | |
|---|---|---|---|---|---|---|---|---|
| Example | N-Phenyl maleimide | Acrylonitril | A (Note 1) | B (Note 2) | Purity of N-phenyl maleimide | Appearance of solution | Purity of N-phenyl maleimide | Appearance of solution |
| 15 | 120 | 100 | 0.2 g | 0.01 g | 99.85 | Clear | 99.85 | Clear |
| 16 | 200 | " | " | " | " | " | " | " |
| 17 | 250 | " | 0.25 | 0.02 | " | " | " | " |

Note 1 A: Triethylene glycol bis [3-(3-t-butyl-5-methyl-4-hydroxyphenyl) propionate]
Note 2 B: P-Methoxyphenol

EXAMPLE 18

A cylindrical tank measuring 5.6 m in length and 2.2 m in inside diameter, having an inner volume of 20 m$^3$, and provided with nozzles 3 inches in inside diameter one each in the central part of the upper side and on the lower end was charged with 8 tons of N-phenyl maleimide adjusted to the following attributes and 0.4 kg of p-methoxyphenol. The N-phenyl maleimide used herein was the same as that of Example 1.

TABLE 1

| | Polymerization inhibitor | Amount (% by weight based on solution) | Before Standing Purity of N-phenyl maleimide (% by weight) | Appearance of solution | After Standing Purity of N-phenyl maleimide (% by weight) (Note 1) | Appearance of solution |
|---|---|---|---|---|---|---|
| Example 2 | Triethylene glycol-bis [3-(3-butyl-5-methyl-4-hydroxyphenyl)propionate] | 0.001 | 99.8 | Clear | 99.8 | Clear |
| Example 3 | Triethylene glycol-bis [3-(3-butyl-5-methyl-4-hydroxyphenyl)propionate] | 0.01 | " | ", | " | " |
| Example 4 | Triethylene glycol-bis [3-(3-butyl-5-methyl-4-hydroxyphenyl)propionate] | 0.1 | " | " | " | " |
| Example 5 | 1,6-Hexanediol-bis [3-(3,5-di-t-butyl-4-hydroxylphenyl)propionate] | 0.05 | " | " | " | " |
| Example 6 | 2,4-Bis-(n-octylthio)-6-(4-hydroxy-3,5-di-t-butylanilino)-1,3,5-triazine | " | " | " | " | " |
| Example 7 | Pentaerythritol tetrakis [3-(3,5-di-t-butyl-4-hydroxyphenyl)propionate] | " | " | ". | " | " |
| Example 8 | 2,2-Thio-diethylenebis [3-(3,5-di-t-butyl-4-hydroxyphenyl)propionate] | " | " | " | " | " |
| Example 9 | Octadecyl-3-(3,5-di-t-butyl-4-hydroxyphenyl) propionate] | " | " | " | " | " |
| Example 10 | 2,2-Thiobis(4-methyl-6-t-butylphenol) | " | " | " | " | " |
| Example 11 | N,N'-hexamethylenebis (3,5-di-t-butyl-4-hydoxy hydrocinnasmide) | " | " | " | " | " |
| Example 12 | 3,5-di-t-butyl-4-hydroxy-benzylphosphate-diethyl ester | " | " | " | " | " |
| Example 13 | 1,3,5-trimethyl-2,4,6-tris (3,5-di-t-butyl-4-hydroxybenzyl)benzene | " | " | " | " | " |
| Example 14 | Tris-(3,5-di-t-butyl-4-hydroxybenzyl)-isocyanurate | " | " | " | " | " |
| Control 1 | None | 0 | 99.8 | Clear | 92.8 | Turbid |

Note 1
Reduced to a value containing no polymerization inhibitor

EXAMPLES 15 TO 17

Solutions were prepared by invariably using N-phenyl maleimide adjusted to the following composition

| Attributes of N-phenyl maleimide | |
|---|---|
| (1) Shape | Flakes |

-continued

| Attributes of N-phenyl maleimide | | |
|---|---|---|
| (2) Particle diameter distribution | No more than 1 mm | 10% |
| | 1 to 4 mm | 90% |
| (3) Average particle diameter | 2 mm | |

The packing density of the tank was 0.5 ton/m³ and the void space inside the tank was about 4 m³. To the contents of the tank, 8 tons of acrylonitrile heated to 60° C. was added via the liquid inlet nozzle disposed in the upper part of the tank. Then, after 30 minutes following this addition, the solution was withdrawn from the tank via the liquid discharge nozzle disposed at the lower end of the tank. At this time, the liquid temperature of the tank was 23° C. Subsequently, the acrylonitrile solution was heated to 50° C. with a heat exchanger possessing a heat transfer area of 30 m² and circulated back into the tank interior via the lower nozzle of the tank. The amount of circulation of this solution was 40 tons/hr, indicating that the solution was circulated through the tank interior at a rate of 2.5 times per hour. When N-phenyl maleimide fed to the tank was thoroughly dissolved, the saturated solution temperature of this solution was 26° C. When this operation was continued for 2 hours, the N-phenyl maleimide was in a thoroughly dissolved state. Thus, there was obtained a yellow clear acrylonitrile N-phenyl maleimide solution.

By ultraviolet absorption spectrometry, this solution was found to have a concentration of 50% by weight, indicating that the N-phenyl maleimide was thoroughly dissolved therein. During the dissolution of the N-phenyl maleimide, the occurrence of minute particles of N-phenyl maleimide was not observed at all.

EXAMPLE 19

A cylindrical tank measuring 5.6 m in length and 2.2 m inside diameter, having an inner volume of 20 m³, and provided with nozzles 3 inches in inside diameter one each in the upper and lower ends thereof was charged with 8 tons of N-phenyl maleimide adjusted to the following attributed and 0.4 kg of p-methoxy phenol. The N-phenyl maleimide used here was the same as that of Example 2.

| Attributes of N-phenyl maleimide | | |
|---|---|---|
| (1) Shape | Flakes | |
| (2) Particle diameter distribution | No more than 1 mm | 10% |
| | 1 to 4 mm | 90% |
| (3) Average particle diameter | 2 mm | |

The packing density of the tank was 0.5 ton/m³ and the void space of the tank was about 4 m³. To the interior of the tank, 8 tons of acrylonitrile heated to 60° C. was introduced via the lower liquid inlet nozzle. Then, after 30 minutes following the addition of the heated acrylonitrile, the solution was withdrawn from the tank via the upper liquid discharge nozzle. At this time, the liquid temperature of the tank was 23° C. Subsequently, the acrylonitrile solution was heated to 50° C. with a heat exchanger having a heat transfer area of 30 m² and circulated back into the tank via the lower liquid inlet nozzle. The amount of the circulation was 40 tons/hr, indicating that the solution was circulated through the interior of the tank at a rate of 2.5 times per hour. When the N-phenyl maleimide was thoroughly dissolved, the saturated solution temperature of this solution was 26° C. When this operation was continued for 2 hours, the N-phenyl maleimide was in a thoroughly dissolved state. Consequently, there was obtained a yellow clear acrylonitrile N-phenyl maleimide solution. By ultraviolet adsorption spectrometry, this solution was found to have a concentration of 50% by weight, indicating that the N-phenyl maleimide was thoroughly dissolved therein. During the course of dissolution of N-phenyl maleimide, the occurrence of minute particles of N-phenyl maleimide was not observed at all.

What is claimed is:

1. An acrylonitrile maleimides solution composition of highly desirable shelf life, having the acid component in said acrylonitrile maleimides solution adjusted to a level of no more than 0.3% by weight based on the amount of said maleimides contained in said solution and having a polymerization inhibitor in said solution adjusted to a level in the range of 0.0001 to 1% by weight based on the amount of said solution.

2. A composition according to claim 1, wherein the concentration of said maleimides is in the range of 30 to 90% by weight.

3. A composition according to claim 2, wherein the amount of said acid component is no more than 0.2% by weight based on the amount of said maleimides contained in said solution.

4. A composition according to claim 1, wherein said polymerization inhibitor is at least one member selected from the group consisting of methoxybenzoquinone, p-methoxyphenol, phenothiazine, hydroquinone, alkylated diphenylamines, methylene blue, tert-butyl catechol, tert-butyl hydroquinone, dialkyldithiocarbamates, copper salicylate, thiodipropionic esters, mercaptobenzimidazole, triphenyl phosphites, alkyl phenols, alkyl bisphenols, 2,4-bis(n-octylthio)-6-(4-hydroxy-3,5-di-t-butylanilino)-1,3,5-triazine, 2,2'-thiobis-(4-methyl-6-t-butylphenol), and triethylene glycolbis-[3-(3-t-butyl-5-methyl-4-hydroxyphenyl)propionate].

5. A composition according to claim 4, wherein said polymerization inhibitor is incorporated in an amount in the range of 0.001 to 0.5% by weight based on the amount of said solution.

6. A method for the production of an acrylonitrile maleimides solution of highly desirable shelf life, which method comprises having the acid component in said acrylonitrile maleimides solution adjusted to a level of no more than 0.3% by weight based on the amount of said maleimides contained in said solution and having a polymerization inhibitor in said solution adjusted to a level in the range of 0.0001 to 1% by weight based on the amount of said solution.

7. A method for the production of a solution of maleimides in acrylonitrile, which comprises placing solid maleimides in a substantially airtight closed container
   said container being packed with said maleimides to a density in the range of 0.2–0.8 ton/m³ and being provided with a circulating means, an outflow means and an inflow means comprising a liquid circulating nozzle,
   heating a acrylonitrile or a solution of maleimides in acrylonitrile to a temperature level about 10° to 30° C. higher than the temperature at which the desired concentration of maleimides in the solution to be prepared, becomes saturated,
   and circulating said heated acrylonitrile solution in the presence of a polymerization inhibitor, the amount of said solution to be circulated during the dissolution of maleimides being set at a level such that the liquid content of the dissolution tank circulates from 0.1 to 10 times per hour through said solid maleimides via said nozzle thereby dissolving said maleimides.

8. A method according to claim 7, wherein said polymerization inhibitor is incorporated in an amount in the range of 0.0001 to 1% by weight based on the amount of said maleimides.

9. A method according to claim 8, wherein the temperature of heating of acrylonitrile is in the range of 10° to 70° C.

10. A method according to claim 8, wherein the concentration of said maleimides is in the range of 30 to 90% by weight.

11. A method according to claim 8, wherein said polymerization inhibitor is at least one member selected from the group consisting of methoxybenzoquinone, p-methoxyphenol, phenothiazine, hydroquinone, alkylated diphenylamines, methylene blue, tert-butyl catechol, tert-butyl hydroquinone, dialkyldithiocarbamates, copper salicylate, thiodipropionic esters, mercaptobenzimidazole, triphenyl phosphites, alkyl phenols, alkyl bisphenols, 2,4-bis(n-octylthio)-6-(4-hydroxy-3,5-di-butylanilino)-1,3,5-triazine, 2,2'-thiobis-(4-methyl-6-t-butylphenol), and triethylene glycolbis-[3,(3-t-butyl-5-methyl-4-hydroxyphenyl) propionate].

12. A method for the production of a solution of maleimides in acrylonitrile, which comprises placing solid maleimides in a substantially airtight closed container said container being packed with said maleimides to a density in the range of 0.2–0.8 ton/m$^3$ and being provided with two liquid circulating nozzles, one of said nozzles being located in the upper and the other in the lower parts thereof, adding acrylonitrile to said solid maleimides in the presence of a polymerization inhibitor, then withdrawing the acrylonitrile solution from said container via the upper nozzle, heating said acrylonitrile solution to a temperature level about 10° to 30° C. higher than the temperature at which the desired concentration of maleimides in the solution to be prepared, becomes saturated, and circulating the heated acrylonitrile solution through said container via the lower nozzle, the amount of said solution to be circulated during the dissolution of maleimides being set at a level such that the liquid content of the dissolution tank circulates 0.1 to 10 times per hour, thereby dissolving said maleimides.

13. A method according to claim 12, wherein said polymerization inhibitor is incorporated in a solution in the range of 0.0001 to 1% by weight based on the amount of said maleimides.

14. A method according to claim 12, wherein the temperature of heating of acrylonitrile is in the range of 10° to 70° C.

15. A method according to claim 14, wherein the concentration of said maleimides is in the range of 30 to 90% by weight.

16. A method according to claim 12, wherein said polymerization inhibitor is at least one member selected from the group consisting of methoxybenzoquinone, p-methoxyphenol, phenothiazine, hydroquinone, alkylated diphenylamines, methylene blue, tert-butyl catechol, tert-butyl hydroquinone, dialkyldithiocarbamates, copper salicylate, thiodipropionic esters, mercaptobenzimidazole, triphenyl phosphites, alkyl phenols, alkyl bisphenols, 2,4-bis(n-octylthio)-6-(4-hydroxy-3,5-di-butylanilino)-1,3,5-triazine, 2,2'-thiobis-(4-methyl-6-t-butylphenol), and triethylene glycolbis-[3,(3-t-butyl-5-methyl-4-hydroxyphenyl) propionate].

17. A method for the production of an acrylonitrile maleimides solution, which method comprises providing preliminarily loosened solid maleimides in an airtight closed container or crushing solid maleimides in said airtight closed container said container being a hopper type container provided with inlet and outlet nozzles for an inert gas, and inlet and discharge outlets for said maleimides said discharge outlet having an airtight connection to an adjacent dissolution tank, providing a substantially inert atmosphere of at least one inert gas selected from the group consisting of nitrogen, carbon dioxide, and argon, to said hopper and said tank, continuously or intermittently introducing said maleimides from said container to said tank in a rate range of 1 to 1000 kg/min. per ton of said acrylonitrile thereby dissolving said maleimides in acrylonitrile therein, said maleimides being dissolved in said acrylonitrile at a temperature in the range of 10° to 70° C.

18. A method for the production of an acrylonitrile maleimides solution, which comprises providing solid maleimides to an airtight closed container and crushing them therein said container being a hopper type container provided with inlet and outlet nozzles for an inert gas, inlet and discharge outlets for said maleimides said discharge outlet having an airtight connection to an adjacent dissolution tank providing a substantially inert atmosphere of at least one inert gas selected from the group consisting of nitrogen, carbon dioxide, and argon, to said hopper and said tank, continuously or intermittently introducing said maleimides from said container to said tank in a rate range of 1 to 1000 kg/min. per ton of said acrylonitrile thereby dissolving said maleimides in acrylonitrile therein, said maleimides being dissolved in said acrylonitrile at a temperature in the range of 10° to 70° C.

* * * * *

UNITED STATES PATENT AND TRADEMARK OFFICE
CERTIFICATE OF CORRECTION

PATENT NO. : 5,128,484
DATED : July 7, 1992
INVENTOR(S) : Kita, et. al.

It is certified that error appears in the above-indentified patent and that said Letters Patent is hereby corrected as shown below:

On the Title page, item [73], Assignee should read -- Nippon Shokubai Kagaku Kogyo Co., Ltd., Osaka, Japan--.

Signed and Sealed this

Seventeenth Day of August, 1993

Attest:

BRUCE LEHMAN

*Attesting Officer*   *Commissioner of Patents and Trademarks*